(12) United States Patent
Tu

(10) Patent No.: US 6,235,024 B1
(45) Date of Patent: May 22, 2001

(54) CATHETERS SYSTEM HAVING DUAL ABLATION CAPABILITY

(76) Inventor: Hosheng Tu, 2151 Palermo, Tustin, CA (US) 92782

( * ) Notice: Subject to any disclaimer, the term of this patent is extended or adjusted under 35 U.S.C. 154(b) by 0 days.

(21) Appl. No.: 09/334,503

(22) Filed: Jun. 21, 1999

(51) Int. Cl.[7] ................................................. A61B 18/18
(52) U.S. Cl. ............................ 606/41; 604/22; 600/439; 600/466
(58) Field of Search .................................. 606/1, 41, 42, 606/169; 600/437, 439, 459, 462, 466; 604/22; 601/2

(56) References Cited

U.S. PATENT DOCUMENTS

| | | | |
|---|---|---|---|
| 4,886,060 | * 12/1989 | Wiksell | ................................. 604/22 |
| 4,936,281 | * 6/1990 | Stasz | ................................. 128/660.03 |
| 5,190,517 | * 3/1993 | Zieve et al. | ............................. 604/22 |
| 5,368,557 | 11/1994 | Nita et al. . | |
| 5,474,530 | 12/1995 | Passafaro et al. . | |
| 5,606,974 | * 3/1997 | Castellano et al. | ............. 128/662.06 |
| 5,676,692 | 10/1997 | Sanghvi et al. . | |
| 5,776,092 | * 7/1998 | Farin et al. | ............................. 604/22 |
| 5,827,204 | 10/1998 | Grandia et al. . | |
| 6,102,908 | * 8/2000 | Tu et al. | ................................. 606/41 |

FOREIGN PATENT DOCUMENTS

0310431 * 4/1989 (EP) .

* cited by examiner

*Primary Examiner*—Michael Peffley (57) ABSTRACT

An improved ablation catheter system comprising an ablation element on a distal section of an elongate catheter tubing, the ablation element having dual capability of radiofrequency ablation and ultrasound ablation, the ablation element comprising an ultrasound transducer, a conductive outer surface and a conductive inner surface, the ablation catheter system further comprising a high frequency energy generator means which has a switching means for switching the ablation operation mode to a radiofrequency ablation mode, an ultrasound ablation mode, or a simultaneous radiofrequency and ultrasound ablation mode.

15 Claims, 5 Drawing Sheets

CATHETERS SYSTEM HAVING DUAL ABLATION CAPABILITY

FIELD OF THE INVENTION

The present invention generally relates to improved constructions for an ablation catheter system. More particularly, this invention relates to an ablation catheter and methods having dual ablation capability of radiofrequency ablation and ultrasound energy ablation for treating tissues and atherosclerosis.

BACKGROUND OF THE INVENTION

An artery is one of the tube-shaped blood vessels that carry blood away from a heart to the body's tissues and organs. An artery is made up of an outer fibrous layer, a smooth muscle layer, connecting tissues and inner lining cells. If arterial walls become hardened due to the accumulation of fatty substances, then blood flow can be diminished. Hardening of the arteries, or loss of vessel elasticity, are termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through an artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or cells to the blood stream.

There are limitations, however, to this technique's application, depending on the extent of the disease, the blood flow through the artery, and the part of the anatomy and the particular vessels involved. Plaque build-up and/or severe re-stenosis recurrence within 6 months is up to 30–40 percent of those treated. Balloon angioplasty can only be characterized as a moderate-success procedure. Recently, a newer technique of inserting a metallic stenting element, e.g. a coronary stent, is used to permanently maintain the walls of the vessel treated at its extended opening state. Vascular stents are tiny mesh or coil tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. The underlying fresh tissue or cells after angioplasty/stenting procedures still pose as a precursor for vessel reclosures, restenosis, or angio-spasm.

One major drawback with angioplasty and/or stenting is that they open up the plaque or the obstruction and expose the underlying collagen or damaged endothelium to the blood flow. Fresh collagen has pro-thrombotic and platelet-affinity properties that are part of body's natural healing processes. Unless the collagen or the damaged endothelium is passivated or modulated, the chances for blood vessel clotting as well as restenosis always exist. Moderate focal heat is known to tighten and shrink the collagen tissue. It is also clinically verified that thermal energy is capable of denaturing the tissue and modulating the collagenous molecules in such a way that treated tissue becomes more resilient. Therefore, it becomes imperative to post-treat vessels walls after the walls are treated with angioplasty, stenting, or atherectomy procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection, to other natural processes.

One type of thermal therapies is radiofrequency (RF) ablation, which requires tissue contact. Another type of thermal therapies is ultrasonic ablation, which can penetrate into a tissue. RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

Other situations may arise where it is advantageous or desirable to combine the benefits of an ultrasound ablation for a deep tissue treatment and a RF current therapy for providing focal thermal energy to the treated tissue. The RF energy can generally penetrate at about a couple of millimeters into the tissue while the ultrasound energy can generally penetrate several millimeters into the tissue. Furthermore, when RF energy is applied to an implanted stent, the stent-contacting tissue is thermally treated while the tissue gap between the stenting members is not well treated. This group of tissue gap can be simultaneously treated by ultrasound energy.

The high frequency ultrasound is the "microwave" of sound. The wavelength of the older, more conventional twenty-kilohertz ultrasound is 7.5 cm. The typical frequency is about 660 kilohertz, which has a wavelength of 2.2 millimeter. These higher frequencies allow higher ultrasonic energy densities of several hundred watts per square centimeter. Several U.S. patents disclose ultrasonic ablation and its application. Examples are U.S. Pat. No. 5,368,557 to Nita et al., U.S. Pat. No. 5,474,530 to Passafaro et al., U.S. Pat. No. 5,606,974 to Castellano et al., U.S. Pat. No. 5,676,692 to Sanghvi et al., and U.S. Pat. No. 5,827,204 to Grandia et al. However, none of the above-identified patents discloses an ablation element having dual ablation capability of ultrasound ablation and radiofrequency ablation.

Therefore, there is an urgent need for an improved ablation catheter system having the dual capability to effectively treat the tissues by using radiofrequency energy for surface treatment and using ultrasound energy for deep treatment to treat a blood vessel or other tissues, such as esophagus, larynx, liver, uterus, urethra and the like.

SUMMARY OF THE INVENTION

In general, it is an object of the present invention to provide a method and an improved ablation catheter system for generating heat, to treat the vascular vessels, or other tissues, such as intestine, colon, urethra, uterine tube, and the like. It is another object of the present invention to provide an ablation catheter having dual ablation capability of radiofrequency ablation mode and ultrasound ablation mode.

It is still another object of the present invention to provide a method and a catheter for monitoring the temperature of the ablated tissue, and to control the temperature by utilizing a temperature controller and/or algorithm. The location of the temperature sensor is preferably at close proximity of an ablation element of the ablation catheter. It is still another object of this invention to provide a method and an ablation catheter for treating atherosclerosis, vascular walls, or tubular cellular tissues of a body by applying RF current through the ablation element to an expandable stent and consequently to the underlying tissues. It is another object to provide an ablation catheter system comprising an ultrasound ablation element to treat the underlying tissue.

A catheter system of the present invention comprises an elongate catheter tubing having a distal section, a distal end, a proximal end, and at least one lumen extending between the distal end and the proximal end. A handle is attached to the proximal end of said elongate catheter tubing, wherein the handle has a cavity.

The catheter system further comprises an ablation element mounted at the distal section of the elongate catheter tubing, the ablation element having a wall with an outer surface and an inner surface, wherein the outer surface is covered with an outer member made of a first electrically conductive material and the inner surface is covered with an inner member made of a second electrically conductive material, and wherein the wall comprises an ultrasound transducer. The ultrasonic transducer is preferably made of a piezoelectric material.

An electrical conducting means has a first and a second electrical wires, wherein the first electrical wire is coupled to the outer member of the ablation element and the second electrical wire is coupled to the inner member of the ablation element. Both the outer member and the inner member are intimately secured to the surfaces of the ultrasound transducer.

In a preferred embodiment, the conductivity of the first electrically conducting material for the outer member is higher than the conductivity of the second electrically conducting material for the inner member. This is to facilitate the radiofrequency ablation using the outer member only because RF requires tissue contact. The inner member and the outer member are made of a process selected from the group consisting of metallic coating, metallic deposition, metallic spraying, and metallic bonding. The inner member and the outer member are made of a material selected from the group consisting of gold, silver, nickel, aluminum, tungsten, platinum, magnesium, and an alloy of their mixtures.

The catheter system further comprises a high frequency energy generator means for providing a radiofrequency energy to the ablation element through a first electrical wire of the electrical conducting means and/or providing an ultrasound energy to the ablation element through both of the first and the second electrical wires of the electrical conducting means. The high frequency spectrum for the high frequency generator means in this patent covers the range from about 50 kHz to approximately 5,000 kHz sufficient to cause tissue ablation, wherein the radiofrequency for the high frequency energy generator means is in the range of 50 kHz to 2,000 kHz, and wherein the ultrasound frequency for the high frequency energy generator means is in the range of 200 kHz to 5,000 kHz. The high frequency energy is provided from the high frequency energy generator means to the ablation element in an operating mode selected from the group consisting of radiofrequency ablation mode, ultrasound ablation mode, and simultaneous radiofrequency and ultrasound ablation mode.

Said catheter system may further comprise a steering mechanism at the handle for controlling deflection of the distal section of the elongate catheter tubing. The catheter system further comprises a temperature sensor mounted at close proximity of the ablation element and an external closed-loop temperature controller, wherein the temperature sensor is adapted for providing temperature signals to said temperature controller for controlling the high frequency energy delivery to the ablation element.

Briefly, heat is generated by supplying a suitable energy source to an ablation element of the catheter system, which comprises dual ablation capability for radiofrequency ablation and ultrasound ablation. A suitable energy source may consist of radiofrequency energy, microwave energy, ultrasonic energy, alternating current energy, or laser energy. The energy may be applied to the stent and consequently to the vessel walls, or cellular tissues, or directly to the target tissue bypassing the stent portion. In radiofrequency ablation operations, a DIP (dispersive indifferent pad) type pad or electrode, that contacts the patient, is connected to the Indifferent Electrode Connector on the RF current generator. Therefore, the RF energy delivery becomes effective when a close circuit from a RF generator through an ablation element of said catheter and a patient, and returning to the RF generator is formed. When using a high frequency current outlet, the generator should be grounded to avoid electrical interference. In ultrasound ablation operations, an ultrasound transducer may be used to generate longitudinal or radial vibrations which create energy for forming channels of different depths and sizes. Heat is controlled by the power of the high frequency energy generator means and by the delivery duration. The standard high frequency energy generator means and its applications through the ablation element means, either radiofrequency ablation or ultrasound ablation, to a patient are well known for one who is skilled in the ordinary art.

The method and ablation catheter system of the present invention has several significant advantages over other known systems or techniques to treat a constricted vessel or even an enlarged vessel. In particular, the ablation catheter system comprising an ablation element having RE ablation and ultrasound ablation capabilities to treat the tissues results in a more efficient therapeutic effect, which is highly desirable in its intended application on the atherosclerosis or constricted vessels.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 5, what is shown is a preferred embodiment of the present ablation catheter system, comprising applying radiofrequency energy and/or applying ultrasonic energy from an ablation element to treat the atherosclerosis, vascular vessels, or other tubular cellular tissues of a patient.

Figure 1:
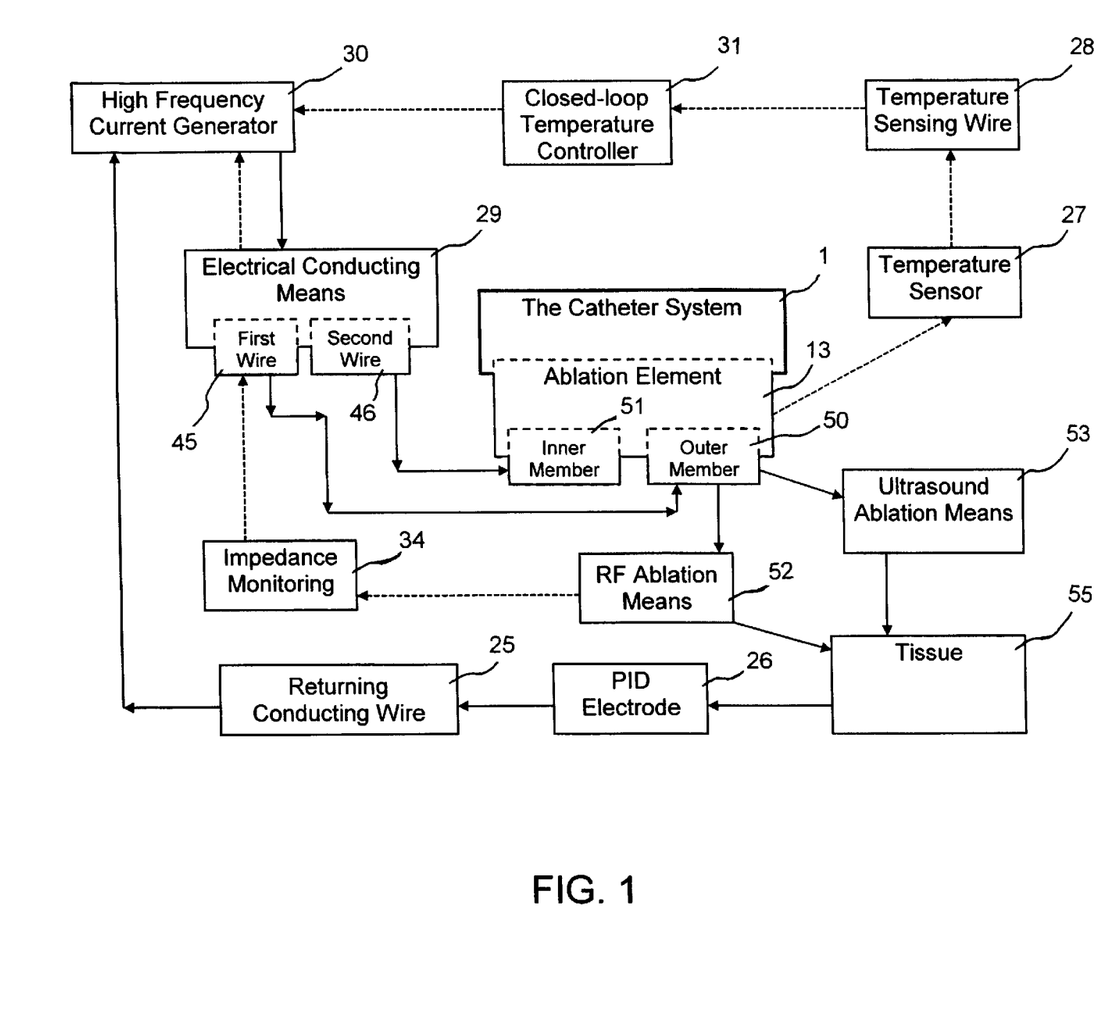
FIG. 1 is a schematic diagram of a treatment method comprising ultrasound and RF ablations in relation to a tissue of a patient.

FIG. 1 shows a schematic diagram of a treatment method comprising ultrasound and RF ablations in relation to a tissue 55 of a patient. A high frequency current or energy generator means 30 is connected to an ablation element 13 of an ablation catheter 1 through an electrical conducting means 29. In one embodiment, the electrical conducting means 29 comprises a plurality of conducting wires 45, 46. The ablation element 13 comprises a wall 47 with an outer surface 48 and an inner surface 49, wherein the outer surface 48 is covered with an outer member 50 made of a first electrically conductive material and the inner surface 49 is covered with an inner member 51 made of a second electrically conductive material, and wherein the wall 47 comprises an ultrasound transducer, which may be made of a piezoelectric material.

The electrical conducting means 29 has a first electrical wire 45 and a second electrical wire 46, wherein the first electrical wire 45 is coupled to the outer member of the outer surface 48 and the second electrical wire 46 is coupled to the inner member of the inner surface 49 of the ablation element 13. The high frequency energy generator means 30 for providing a radiofrequency energy in RF ablation means 52 to the ablation element 13 through a first electrical wire 45 of the electrical conducting means 29 and/or providing an ultrasound energy in ultrasound ablation means 53 to the ablation element 13 through both of the first and the second electrical wires 45, 46 of the electrical conducting means 29.

In another embodiment, the ablation element 13 is to contact the tissue 55 directly or through a stent 56. In an alternate embodiment, the stent 56 is in close contact with the underlying tissue 55. A DIP (dispersive indifferent pad) type pad 26, that contacts the patient, is connected to the Indifferent Electrode Connector on the high frequency generator means 30 through a returning electrical wire 25. Therefore, the high frequency energy delivery becomes effective when a close circuit from a generator 30 through a patient and returning to the generator is formed. Impedance 34 measured from the tissue contact is to ensure good tissue contact for ablation, otherwise the RF power is cutoff when the impedance is unreasonably off the acceptance value. A temperature sensor 27 is used to measure the tissue temperature and is relayed through a temperature sensing wire 28 and a closed-loop temperature controller 31 for controlling the ablative energy delivered. Heat is controlled by the power of the energy delivered and by the delivery duration.

Figure 2:
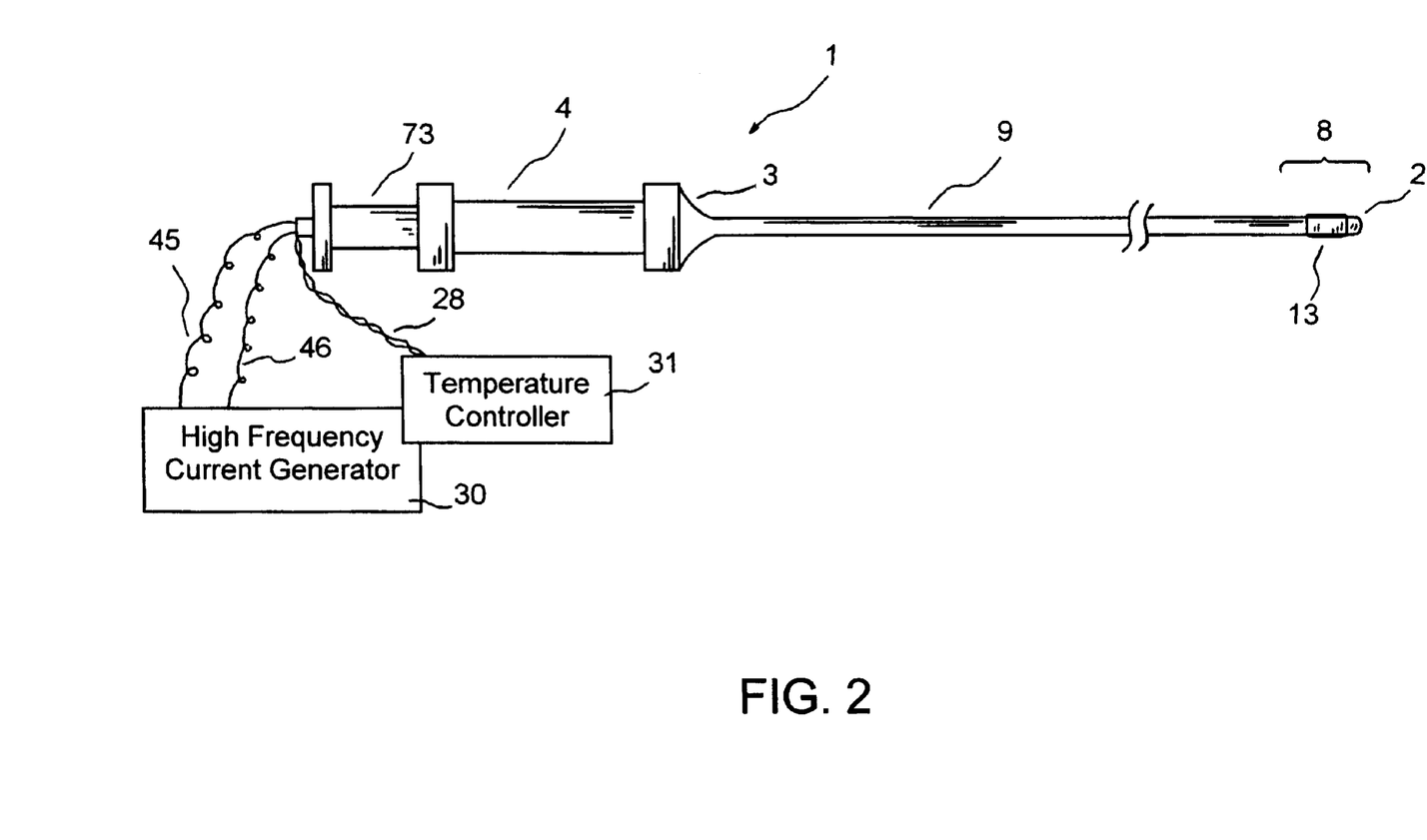
FIG. 2 is an overall view of a preferred ablation catheter system with an ablation element having dual ablation capability, constructed in accordance to the principles of the present invention.

As shown in FIG. 2, the ablation catheter system 1 in the form of an elongate catheter tubular assembly comprises an elongate catheter tubing 9 having a distal section 8, a distal end 2, a proximal end 3, and at least one lumen 10 extending therebetween. A handle 4 is attached to the proximal end 3 of the elongate catheter tubing 9, wherein the handle 4 has a cavity. An ablation element 13 is disposed at the distal section 8.

Figure 3:
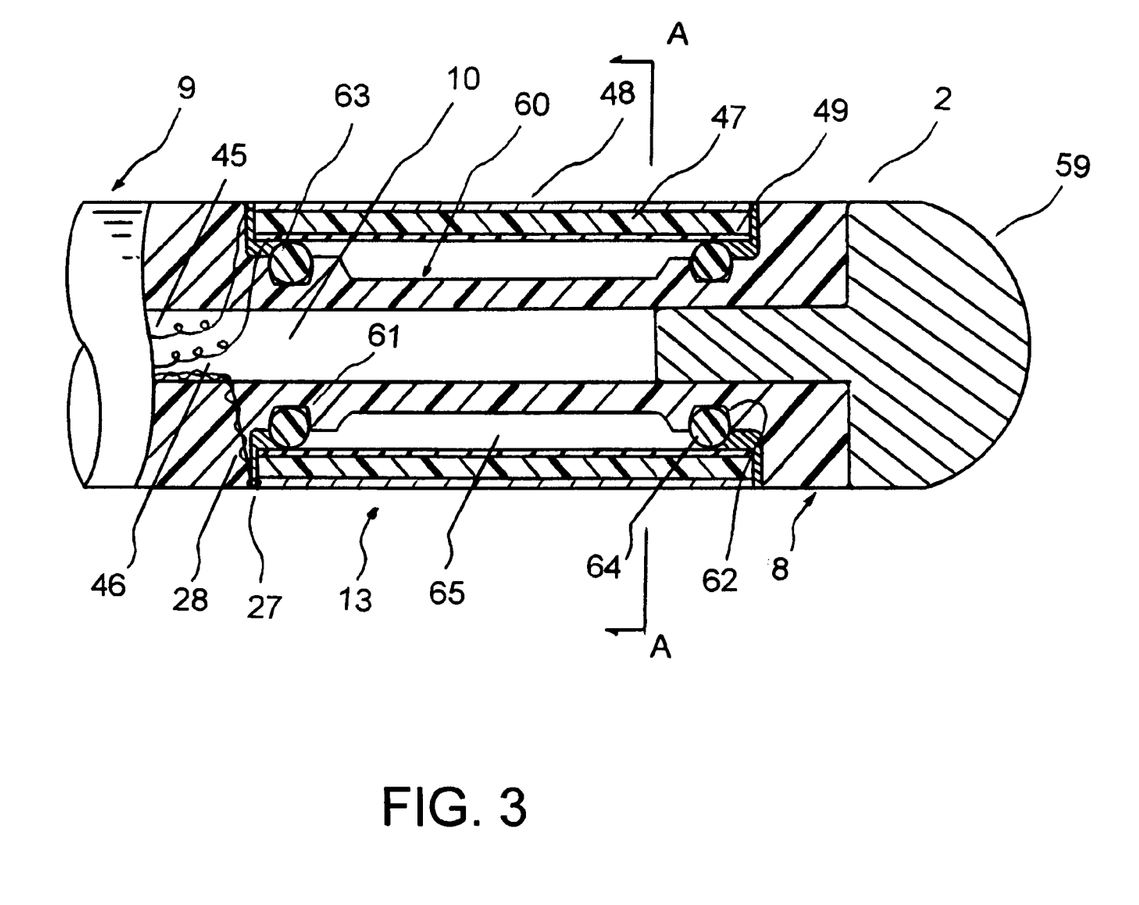
FIG. 3 is a side cross-sectional view of the distal end portion of a preferred ablation catheter, having an ablation element with dual ablation capability.

FIG. 3 shows a side cross-sectional view of the distal end portion of a preferred ablation catheter 1, having an ablation element 13 with dual ablation capability. At least one temperature sensor 27 is mounted at close proximity of the ablation element 13. The ablation element 13 comprises a cylindrical transducer 47 having outer surface 48 and inner surface 49, wherein the outer surface is covered with an outer member made of a first electrically conductive material and the inner surface is covered with an inner member made of a second electrically conductive material.

The inner member and the outer member may be made of a manufacturing process selected from the group consisting of metallic coating, metallic deposition, metallic spraying, metallic bonding, and the like. The inner member and the outer member may be made of a material selected from the group consisting of gold, silver, nickel, aluminum, tungsten, platinum, magnesium, and an alloy of their mixtures. In a preferred embodiment, the conductivity of the first electrically conducting material for the outer member is higher than the conductivity of the second electrically conducting material for the inner member.

It has been noted that piezoelectric transducers may effect a pumping action of fluid through an associated orifice or opening due to the movement of the transducer. Fluid entry into the interior of an ablation catheter is undesired. A cap 59 at the distal end 2 of the elongate catheter tubing 9 is to prevent water leakage.

In general, the ablation element 13 is mounted to a mounting base 60 and the mounting base is part of the distal section 8 of the elongate catheter tubing 9. Said mounting base 60 has two annual O-ring retention grooves 61, 62. The ablation element 13 is then mounted over the O-rings 63, 64 which are positioned inside said O-ring retention grooves 61 and 62. The O-rings may be made of low Durometer material such as silicone or polyurethane. The space 65 between the mounting base 60 and the ablation element 13 is so designed and spaced for absorbing the vibration from the piezoelectric transducer 47. In one particular embodiment, the space 65 is in an essentially vacuum state because ultrasound cannot transfer through a vacuum.

A high frequency current generator means 30 is part of the ablation catheter system 1, wherein an electrical conducting means 29 is coupled from the generator 30 to the ablation element 13. The high frequency energy generator means 30 may comprise a switch means for switching high frequency energy to radiofrequency spectrum, ultrasound frequency spectrum, or radiofrequency/ultrasound frequency overlapped spectrum. This switch means is an operator-initiated action to the appropriate ablation mode selected from the group consisting of radiofrequency ablation mode, ultrasound ablation mode, and simultaneous radiofrequency and ultrasound ablation mode. In each mode, the energy delivery may be continuous, pulsed, programmed, and the like.

Figure 4:
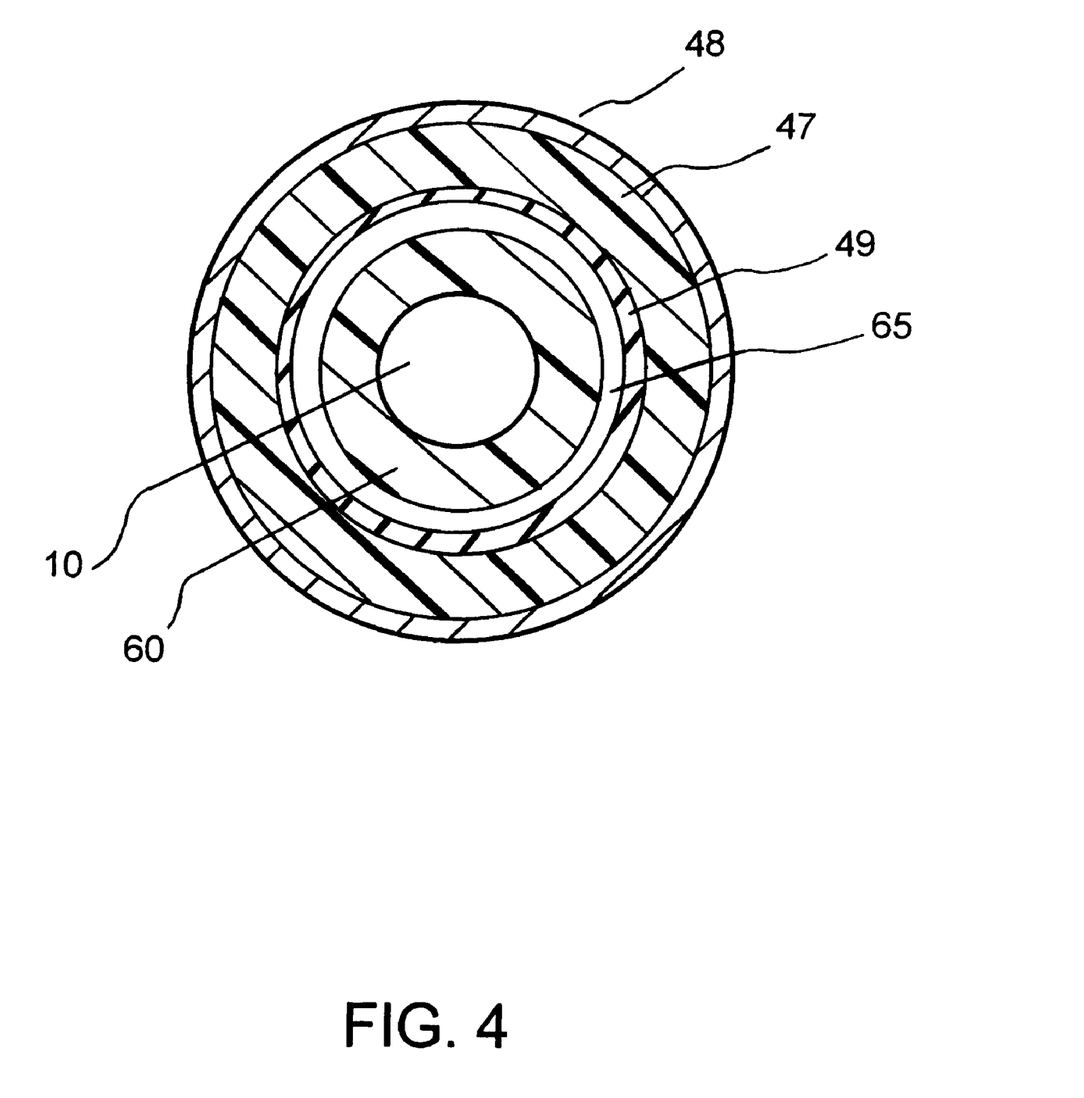
FIG. 4 is a front cross-sectional view of the distal end portion of a preferred ablation catheter, section A—A of FIG. 3, having an ablation element with dual ablation capability.

FIG. 4 shows a front cross-sectional view of the distal end portion of a preferred ablation catheter, section A—A of FIG. 3, having an ablation element with dual ablation capability. The ablation element 13 includes the outer surface 48, the transducer 47 and the inner surface 49. The first insulated electrical wire 45 of the electrical conducting means 29 is at one end coupled to the outer surface 48 and at another end coupled to the high frequency generator means 30.

On one hand, said electrical circuit from the generator 30 through the wire 45 to the outer surface 48 constitutes a portion of the radiofrequency ablation mode, while the remaining portion of the circuit comprises a tissue 55, a PID pad 26, a returning wire 25 and the generator 30. The second insulated electrical wire 46 of the electrical conducting means 29 is at one end coupled to the inner surface 49 and at another end coupled to the generator 30. On the other hand, both electrical circuits including 30-to-45-to-48 and 30 to-46-to-49 and the transducer 47 constitute the ultrasound ablation mode.

The catheter system of the present invention further comprises a steering mechanism 73 at the handle 4 for controlling deflection of the distal tip section 8 of the elongate catheter tubing 9. Usually a rotating ring or a push-pull plunger is employed in the steering mechanism. In another embodiment, the steerable ablation catheter comprises bi-directional deflection of the distal tip section perpendicular to the catheter tubing. In an exemplary embodiment, the means for deflecting the distal portion of the catheter comprises at least one steering wire along with a flat wire. Said steering wires are attached to radially offset locations at the distal end of the deflectable portion of the catheter tubing whereas at least a flat wire radially offset the steering wires, and means at the proximal end of the tubing for selectively applying tension to the steering wires to cause deflection of the deflectable tip section. In some cases, the function of a flat wire can be substituted by a spring coil that is stationary at its proximal end with respect to the tubing. Usually the means for selectively applying tension comprises a handle, and means for applying tension to the steering wire comprises a rotatable ring or a push-pull button disposed on the handle, the ring or button being coupled to the proximal end of a steering wire. A variety of other tensions applying mechanisms, such as joysticks, may also be employed. The steering mechanism and its construction in a catheter is well known to one who is skilled in the art.

Figure 5:
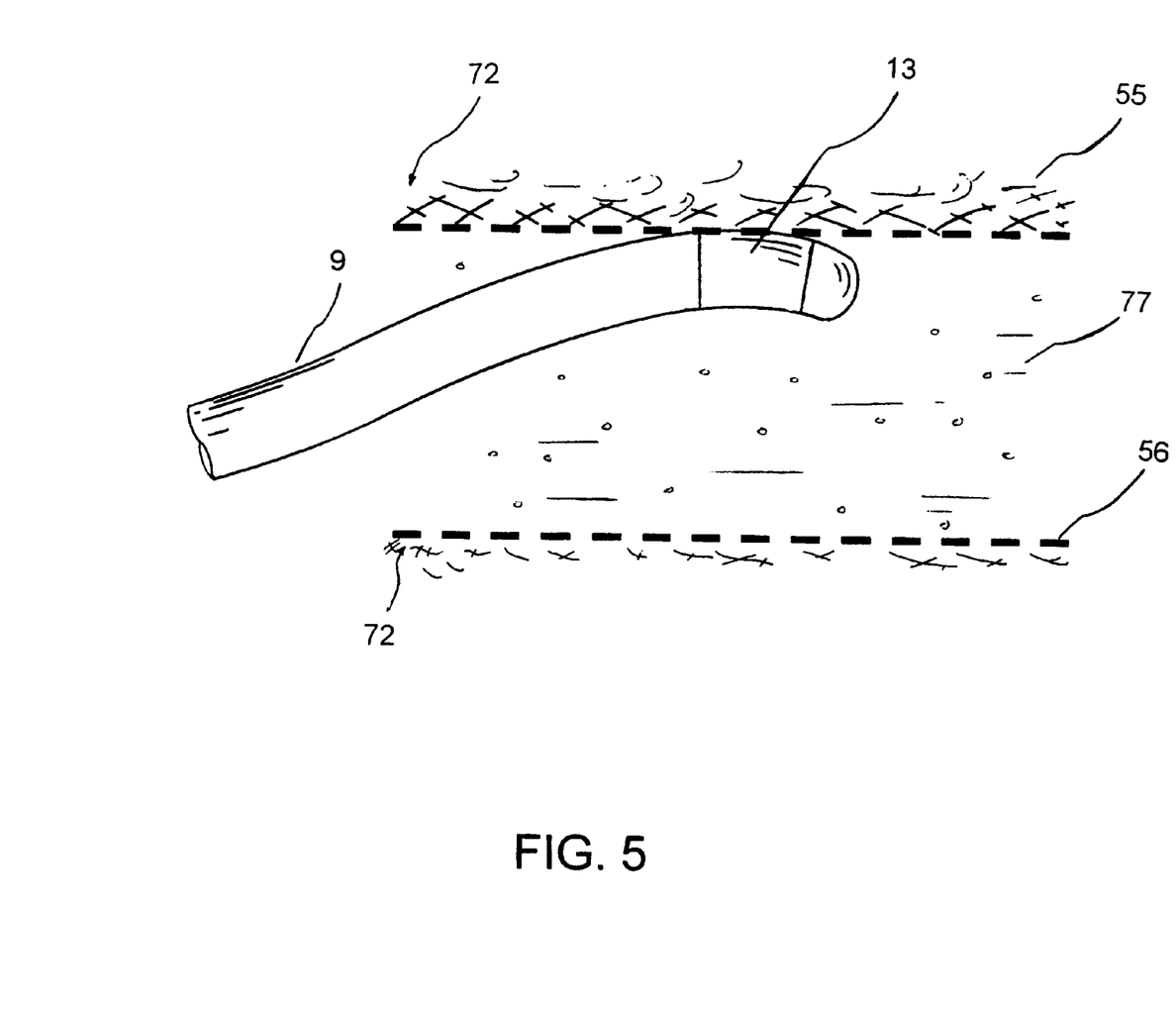
FIG. 5 is a simulated view of placing an ablation catheter of the present invention in contacting an implanted stent inside a blood vessel.

FIG. 5 shows a simulated view of placing an ablation catheter 1 of the present invention in contacting an implanted stent 56 inside a blood vessel. For illustration purposes, after a stent is deployed inside a blood vessel 72, an ablation catheter having an ablation element 13 with dual ablation capability is placed to contact the stent 56 at an appropriate location. At this time, blood stream 77 continues to flow inside the blood vessel 72. Depending on a physician's decision, radiofrequency energy can be delivered to the stent 56 and subsequently to the underlying tissue 55 for direct stent-contacted tissue treatment. Similarly, ultrasound energy can be delivered to the surrounding tissue for indirect deep tissue treatment.

The principle for ultrasound ablation is that the mechanical energy resulting from transducer vibration is being converted to a waveform that radiates energy away from the disturbance. Mechanical vibrations become vibrating pressure waves, transferring energy to the medium and to objects that the wave contacts. Generally the usable ultrasound frequency is between 18 kHz to 10 MHz. However, the ultrasound frequency much lower than 200 kHz has longer wavelengths and greater amplitude for a given input energy and produce greater disruption of the medium. The greater disruption leads to increased motion and, in a liquid, the very interesting phenomenon of cavitation.

In one embodiment, a method for operating a catheter system of the present invention to treat a tissue, the method comprises the steps of (a) inserting the catheter system to a location of the tissue to be treated; (b) contacting the ablation element of the catheter system against the tissue to be treated; and (c) applying high frequency energy from the high frequency energy generator means to the ablation element to effect ablation on the tissue.

Said method further comprises the high frequency energy generator means having a switching means for switching high frequency energy to radiofrequency spectrum, ultrasound frequency spectrum, or radiofrequency/ultrasound frequency overlapped spectrum. The tissue to be treated may have an implanted stent. The tissue to be treated may be selected from the group consisting of a blood vessel, a prostate, a tumor, a liver, a hemorrhage, a uvula, and a polyp.

In another embodiment, a method for operating an ablation catheter to treat a tissue, the ablation catheter comprises an ablation element means for treating the tissue, the ablation element means being mounted at a distal section of the ablation catheter, wherein the ablation element means comprises dual ablation capability of radiofrequency ablation mode and ultrasound ablation mode. The method may comprise the steps of (a) inserting the ablation catheter to a location of the tissue to be treated; (b) contacting the ablation element means of the ablation catheter against the tissue to be treated; and (c) activating the ablation element means to effect tissue treatment by connecting the ablation element means to an external high frequency energy generator means through electrical conducting means for transmitting the ablation energy. Said method for operating an ablation catheter to treat a tissue may further comprise an ablation mode of the ablation element means selected from the group consisting of a radiofrequency ablation mode, an ultrasound ablation mode, and a simultaneous radiofrequency and ultrasound ablation mode. The method further comprises the high frequency energy generator means having a switching means for switching high frequency energy to radiofrequency spectrum, ultrasound frequency spectrum, or radiofrequency/ultrasound frequency overlapped spectrum. The tissue to be treated may have an implanted stent. The tissue to be treated may be selected from the group consisting of a blood vessel, a prostate, a tumor, a liver, a hemorrhage, a uvula, and a polyp.

In an alternate preferred embodiment, the high frequency energy generator means comprises either one or two generators, wherein each of the two generators can be independently operated.

From the foregoing description, it should now be appreciated that an ablation catheter system for the tubular organs, atherosclerosis, and the treatment of vascular tissues, comprising a combination of dual suitable energy sources has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A catheter system comprising:
    an elongate catheter tubing having a distal section, a distal end, a proximal end, and at least one lumen extending between the distal end and the proximal end;
    a handle attached to the proximal end of said elongate catheter tubing, wherein the handle has a cavity;
    an ablation element mounted at the distal section of the elongate catheter tubing, the ablation element having a wall with an outer surface and an inner surface, wherein the outer surface is covered with an outer member made of a first electrically conductive material and the inner surface is covered with an inner member made of a second electrically conductive material, and wherein the wall comprises an ultrasound transducer;

an electrical conducting means having a first and a second electrical wires, wherein the first electrical wire is coupled to the outer member and the second electrical wire is coupled to the inner member of the ablation element; and a high frequency energy generator means for providing a radiofrequency energy to the ablation element through a first electrical wire of the electrical conducting means.

2. The catheter system of claim 1, wherein the high frequency energy generator means further provides an ultrasound energy to the ablation element through both of the first and the second electrical wires of the electrical conducting means.

3. The catheter system of claim 2, wherein the high frequency energy generator means comprises a switching means for switching high frequency energy to radiofrequency spectrum, ultrasound frequency spectrum, or radiofrequency/ultrasound frequency overlapped spectrum.

4. The catheter system of claim 1, wherein the radiofrequency for the high frequency energy generator means is in the range of 50 kHz to 2,000 kHz.

5. The catheter system of claim 2, wherein the ultrasound frequency for the high frequency energy generator means is in the range of 200 kHz to 5,000 kHz.

6. The catheter system of claim 1, wherein the inner member and the outer member are made of a process selected from the group consisting of metallic coating, metallic deposition, metallic spraying, and metallic bonding.

7. The catheter system of claim 1, wherein the inner member and the outer member are made of a material selected from the group consisting of gold, silver, nickel, aluminum, tungsten, platinum, magnesium, and an alloy of their mixtures.

8. The catheter system as in claim 1 further comprising a steering mechanism at the handle for controlling deflection of the distal section of the elongate catheter tubing.

9. The catheter system of claim 1, wherein the ultrasonic transducer is made of a piezoelectric material.

10. The catheter system of claim 2, wherein the high frequency energy is provided from the high frequency energy generator means to the ablation element in an operating mode selected from the group consisting of a radiofrequency ablation mode, an ultrasound ablation mode, and a simultaneous radiofrequency and ultrasound ablation mode.

11. The catheter system as in claim 2, further comprising a temperature sensor mounted at close proximity of the ablation element and an external closed-loop temperature controller, wherein the temperature sensor is adapted for providing temperature signals to the closed-loop temperature controller for controlling the high frequency energy delivery to the ablation element.

12. A method for operating a catheter system to treat a tissue, the catheter system comprising an elongate catheter tubing having a distal section, a distal end, a proximal end, and at least one lumen extending between the distal end and the proximal end; a handle attached to the proximal end of said elongate catheter tubing, wherein the handle has a cavity; an ablation element mounted at the distal section of the elongate catheter tubing, the ablation element having a wall with an outer surface and an inner surface, wherein the outer surface is covered with an outer member made of a first electrically conductive material and the inner surface is covered with an inner member made of a second electrically conductive material, and wherein the wall comprises an ultrasound transducer; an electrical conducting means having a first and a second electrical wires, wherein the first electrical wire is coupled to the outer member and the second electrical wire is coupled to the inner member of the ablation element; and a high frequency energy generator means for providing a radiofrequency energy to the ablation element through a first electrical wire of the electrical conducting means;

the method comprising the steps of:
(a) inserting the catheter system to a location of the tissue to be treated;
(b) contacting the ablation element of the catheter system against the tissue to be treated; and
(c) applying high frequency energy from the high frequency energy generator means to the ablation element to effect ablation on the tissue.

13. The method for operating a catheter system to treat a tissue as in claim 12, the method further comprises the high frequency energy generator means having a switching means for switching high frequency energy to radiofrequency spectrum, ultrasound frequency spectrum, or radiofrequency/ultrasound frequency overlapped spectrum.

14. The method for operating a catheter system to treat a tissue as in claim 13, wherein the tissue to be treated has an implanted stent.

15. The method for operating a catheter system to treat a tissue as in claim 13, wherein the tissue to be treated is selected from the group consisting of a blood vessel, a prostate, a tumor, a liver, a hemorrhage, an uvula, and a polyp.

* * * * *